US005498233A

United States Patent [19]

Stojanović

[11] Patent Number: 5,498,233

[45] Date of Patent: Mar. 12, 1996

[54] DEVICE FOR THERAPEUTIC TREATMENT OF SPINE SYSTEM

[76] Inventor: Branislav Stojanović, D. Stojanovića 6, 21000 Novi Sad, Yugoslavia

[21] Appl. No.: 322,060

[22] Filed: Oct. 12, 1994

Related U.S. Application Data

[63] Continuation of Ser. No. 855,772, Mar. 23, 1992, abandoned.

[30] Foreign Application Priority Data

Mar. 22, 1991 [YU] Yugoslavia ........ 505/91

[51] Int. Cl.[6] ........ A61F 5/02

[52] U.S. Cl. ........ 602/19; 602/18; 128/845

[58] Field of Search ........ 128/907, 845; 606/201, 204, 240; 602/13, 18, 19; 600/9, 12, 13, 14, 15; 482/105; 2/92

[56] References Cited

U.S. PATENT DOCUMENTS

| | | | |
|---|---|---|---|
| 2,447,698 | 8/1948 | Haberer . | |
| 3,605,731 | 9/1971 | Tigges | 128/845 |
| 4,230,099 | 10/1980 | Richardson | 606/240 |
| 4,411,258 | 10/1983 | Pujals, Jr. | 606/204 |
| 4,716,898 | 1/1988 | Chauve et al. | 606/204 |
| 4,760,842 | 8/1988 | Holmes | 606/240 |
| 5,007,633 | 4/1991 | Lemire | 602/19 |
| 5,035,017 | 7/1991 | Komuro | 600/9 |
| 5,048,509 | 9/1991 | Grundei et al. | 602/18 |
| 5,120,288 | 6/1992 | Sinaki | 602/19 |
| 5,140,995 | 8/1992 | Uhl | 2/92 |
| 5,267,947 | 12/1993 | James et al. | 602/19 |
| 5,290,307 | 3/1994 | Choy | 606/240 |

FOREIGN PATENT DOCUMENTS

| | | | |
|---|---|---|---|
| 2187284 | 10/1987 | France . | |
| 120697 | 5/1901 | Germany | 128/78 |
| 2128410 | 12/1972 | Germany | 128/78 |
| 2334500 | 1/1975 | Germany | 128/78 |
| 2506647 | 10/1976 | Germany | 128/78 |
| 1120997 | 10/1984 | U.S.S.R. | 128/78 |
| 2193429 | 2/1988 | United Kingdom | 2/92 |
| 8605091 | 9/1986 | WIPO . | |

*Primary Examiner*—Richard J. Apley
*Assistant Examiner*—Jeanne M. Clark
*Attorney, Agent, or Firm*—Graham & James

[57] ABSTRACT

A device for energetic activation of spine system includes a segment 1 comprising numerous bulges 2 combined with grooves 3. Numerous grooves 4 are disposed on the lateral side of a bulge 2. Two grooves 6 are placed on the upper side, between each third pair of bulges 2. Two concentrically placed cylindrical outlets 5 are disposed on the front side of each outlet 2. A horizontally placed outlet 7 with two cylindrical outlets 8 and a pair of holes 9 are disposed on the front side of the segment 1. An identical outlet 10 with holes 9, 11 is disposed on the back side of the segment 1. Numerous outlets 12 in the form of lines and dots are disposed over the whole surface of the lower side of the segment 1.

7 Claims, 3 Drawing Sheets

DEVICE FOR THERAPEUTIC TREATMENT OF SPINE SYSTEM

This is a continuation of application Ser. No. 07/855,772 filed on Mar. 23, 1992, now abandoned.

BACKGROUND OF THE INVENTION

1. Field of the Invention

The invention relates to a device applied as a helping device for the spine system 2. Brief Description of the Background of the Invention A technical problem solved by the invention is a construction of a device for the spine system in order to make possible the placement of segments on the body by using segments with numerous protruding elements, bulges, recesses, grooves, and engravings, or for fastening a series of segments, placed in a casing, with fastener straps to the spine of a person during walking, working, etc.

SUMMARY OF THE INVENTION

1. Purpose of the Invention

It is an object of the present invention to provide a device for the spine

It is another object of the present invention to provide a local treatment of the cervical or lumbar part of the spine.

It is yet a further object of the present invention to provide an optimal system for treatment of the whole spine.

These and other objects and advantages of the present invention will become evident from the description which follows.

2. Brief Description of the Invention

A device according to this invention, consists of one or more segments, each of them having numerous protruding elements, bulges and grooves. The protruding elements exhibit on their two ends numerous transversal carved notches and grooves and two grooves on the upper side between every third pair of protruding elements. Each protruding element has, on its front side, two concentrically placed cylindrical outlet projections. Segments are made to be connected with other segments in a row, using corresponding pins and holes. The number of segments in one row depends only on the extent, i.e. the length of spine, i.e. the area surrounding the spine which needs treatment.

The device consists of segments which can be used individually for local treatment of the cervical or lumbar part of the spine, or in a row, when it represents an optimal system for treatment of the whole spine.

The invention device may be activated in its original embodiment without the casing by placement onto a lying body, or by fastening the invention device within the casing with belts to a body of a person when the person is in an upright, sitting, lying, or walking position.

The novel features which are considered as characteristic for the invention are set forth in the appended claims. The invention itself, however, both, as to its construction and its method of operation, together with additional objects and advantages thereof, will be best understood from the following description of specific embodiments when read in connection with the accompanying drawings.

BRIEF DESCRIPTION OF THE DRAWINGS

In the accompanying drawings, in which are shown several of the various possible embodiments of the present invention.

DESCRIPTION OF INVENTION AND PREFERRED EMBODIMENT

Figure 1:
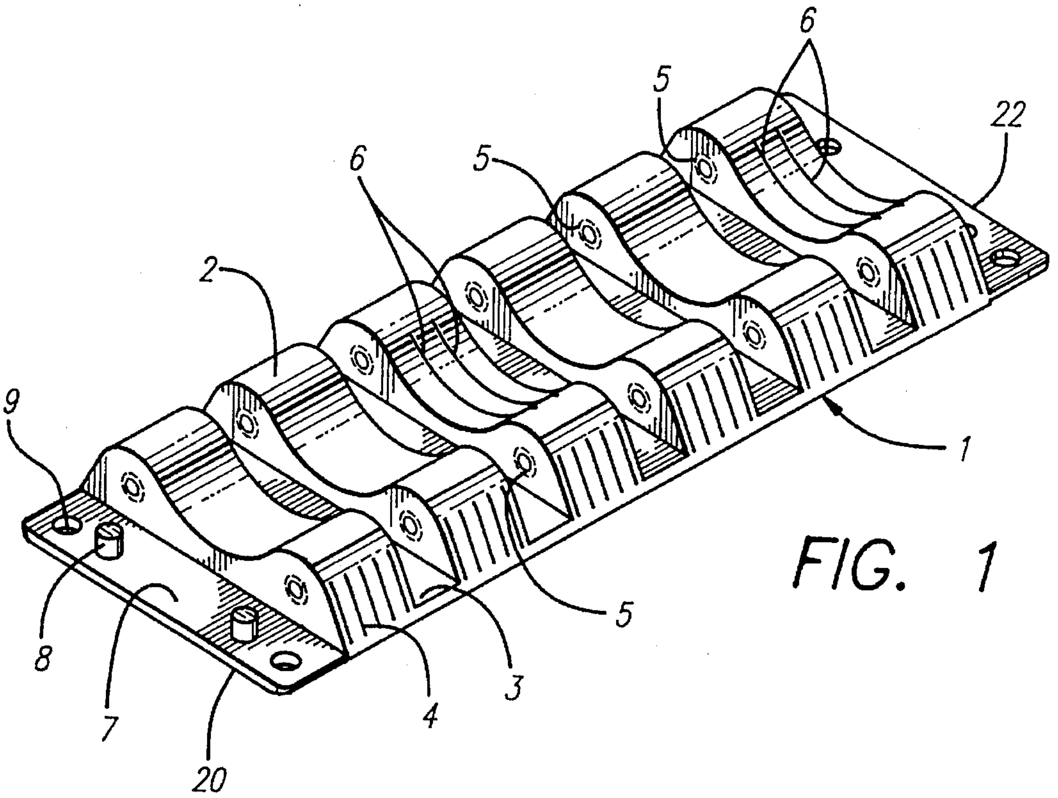
FIG. 1 illustrates a perspective top view onto a device for energetic activation of a spine system.
Figure 2:
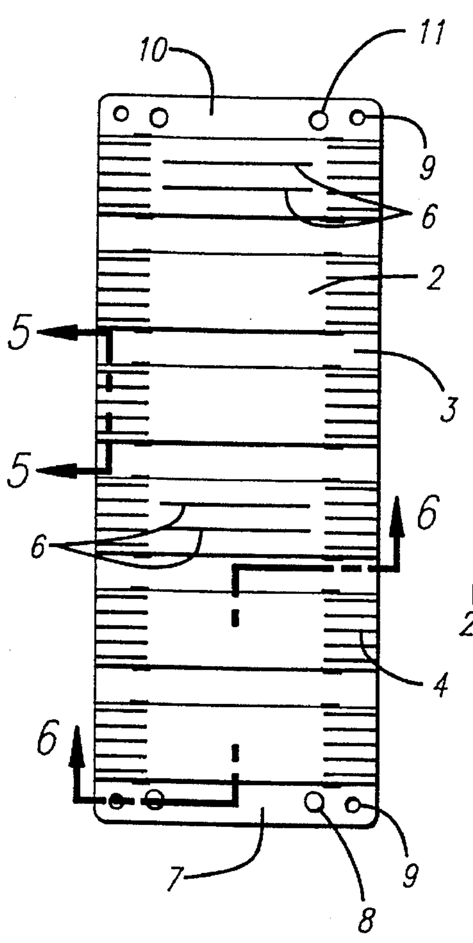
FIG. 2 illustrates a planar view of the invention device.
Figure 3:
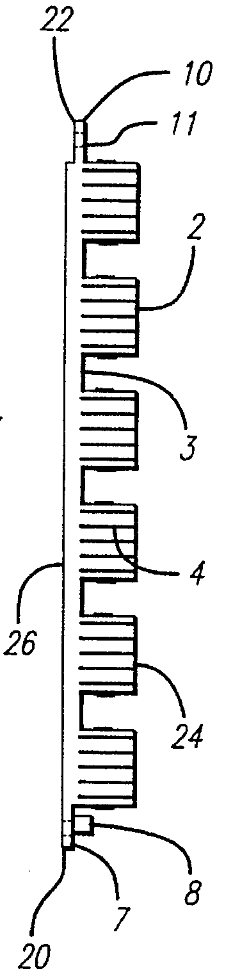
FIG. 3 illustrates a side view of the invention device.
Figure 5:
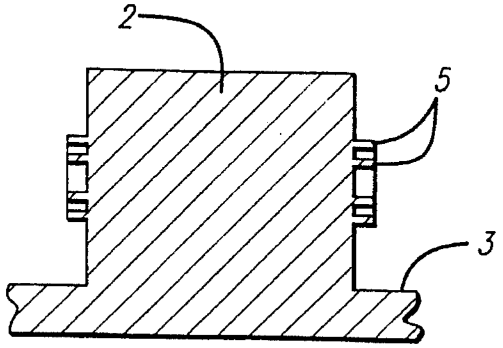
FIG. 5 illustrates a cross-sectional view of the invention device along section line B—B of FIG. 2.
Figure 6:
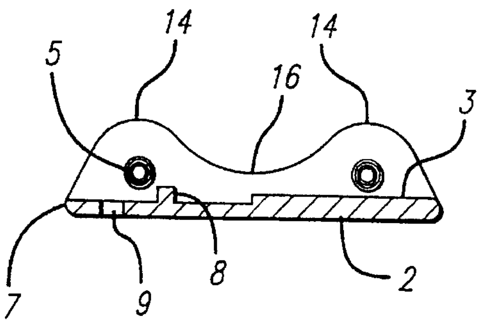
FIG. 6 illustrates a cross-sectional view of the invention device along section line A—A of FIG. 2.

The invention device for therapeutic treatment of a spine consists of one or more segments 1. As illustrated in FIG. 1, a segment 1 exhibits a plurality of protruding elements 2 and recessed surfaces 3 disposed on a first face 24 (FIG. 3) of the segment 1. The two ends of each protruding element 2 exhibit on their outer end surface a plurality of carved notches and grooves (engravings) 4. The protruding element 2 exhibits an undulating shape, where a peak 14 is formed at each end of the protruding element 2, and where a valley 16 is formed between said two peaks 14 (FIG. 6). As illustrated in FIG. 2, two grooves 6 are disposed in the valley 16 of each third protruding element 2. A cylindrical outlet projection 5, illustrated in FIG. 5, is disposed concentrically in the curve of each peak 14 on the longitudinal faces of the protruding element 2. As illustrated in FIGS. 2 and 3, the first end 20 of the segment 1 forms a first connection strip 7. The connection strip 7 is provided with two cylindrical pins 8 and two holes 9. The second end 22 of the segment 1, disposed opposite to the first end 20, forms a second connection strip 10. The second connection strip 10 is provided with two pairs of holes 9 and 11. When linking two or more segments 1 to each other to form a row 28 of segments, the cylindrical pin 8 of the first connection strip 7 of one segment 1 is in each case placed into the hole 11 of the second connection strip 10 of a following segment 1.

Figure 4:
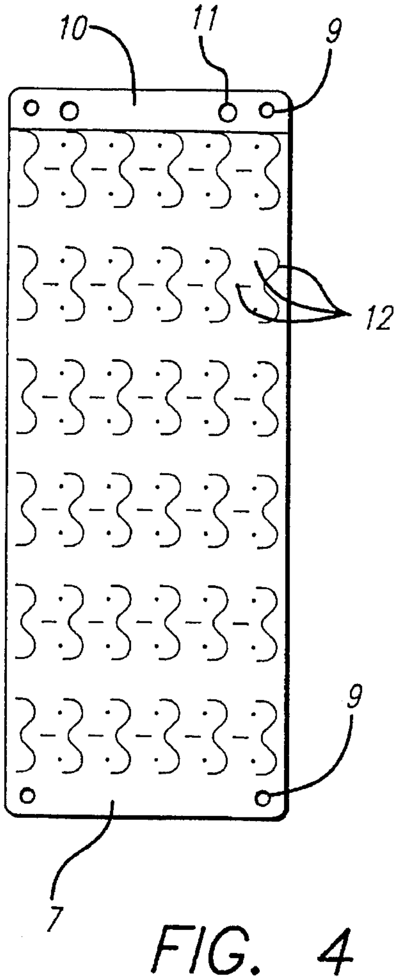
FIG. 4 illustrates a bottom of the invention device.

As illustrated in FIG. 4, the segment 1 exhibits a plurality of projections, notches, and outlets 12, shaped as lines and dots, on the second face 26.

The row 28 of segments 1 can be used for treatment of the whole spine. A desired number of segments 1, forming the row 28, are placed along the spine of a person in a horizontal position, wherein the peaks 14 of the protrusions 2 of the segments 1 are placed on either side of the spine, thereby contouring to the shape of the vertebral column.

Figure 8:
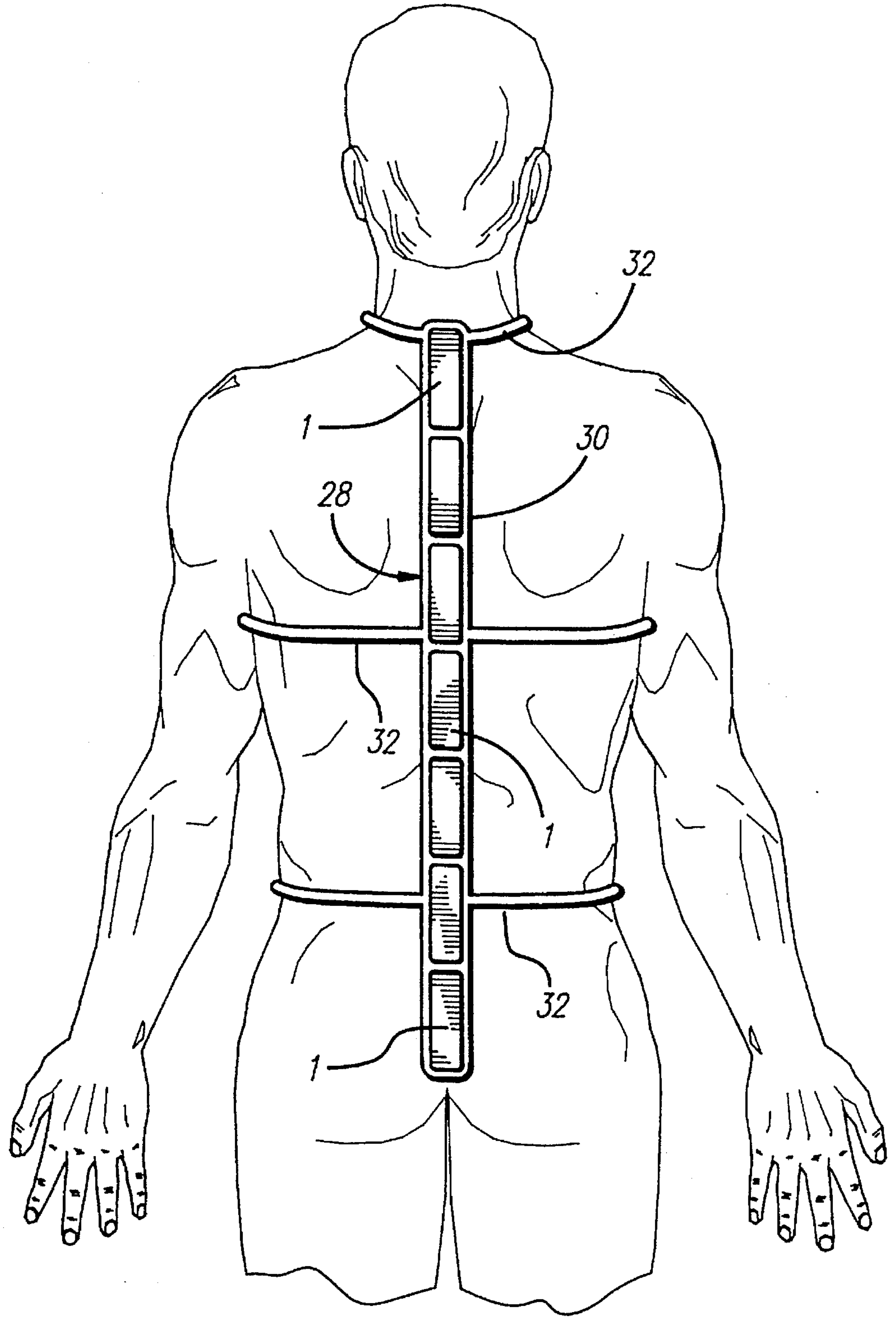
FIG. 8 illustrates an exemplified embodiment of a series of segments disposed in a casing and applied against the length of the spine.

As illustrated in FIG. 8, the row 28 of segments 1 can be placed into a casing 30. The casing 30 includes fastening straps 32 placed at a distance from each other on the two lateral sides of the casing 30. The casing 30, including the row 28 of segments 1, can be placed against the spinal column of a person and fastened to the body of said person by the fastening straps 32, thereby allowing the person to wear the invention device while in an upright position, i.e. the invention device can be worn while the person, wearing the device, can pursue any desired activity. While a person is wearing the invention device, the spine of the person in question is treated correctly.

Figure 7:
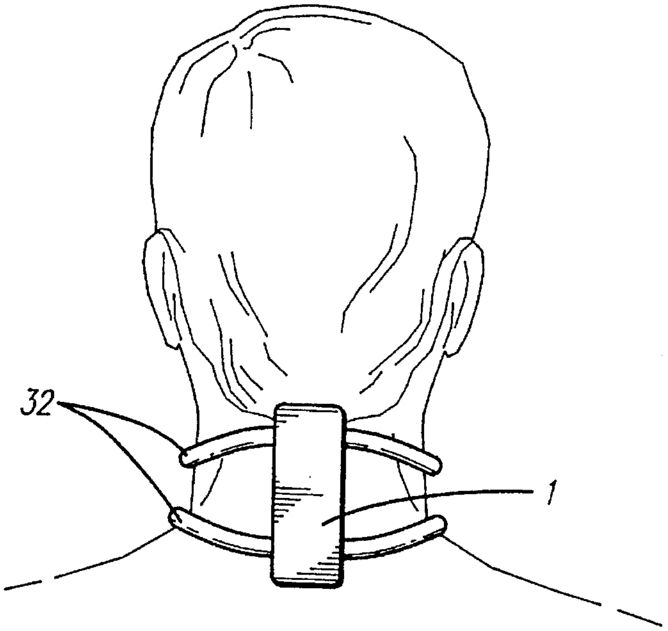
FIG. 7 illustrates an exemplified embodiment of one segment of the invention device placed against the cervical section of the spine.

If it is not necessary to treat the entire length of the spine, it is possible to place the desired number of segments 1 into a casing 30, having a length corresponding to the number of segments 1, and to fasten said casing 30 including the desired number of segments 1, covering the desired part of the spine to be treated, with the fastening straps 32 to the body of the person. An exemplified embodiment of the employment of one segment 1 in a casing 30 is shown in FIG. 7.

It will be understood that each of the elements described above, or two or more together, may also find a useful application in other types of devices.

While the invention has been illustrated and described as embodied in the context of a device for energetic activation of a spine system, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A therapeutic device for being positioned about a user's spine comprising:

a plurality of linkable segments wherein each segment comprises:

a linking means for optionally linking together segments with each other;

a discrete mounting structure elongated in a longitudinal direction wherein said linking means is located on at least one end of the mounting structure in the longitudinal direction; and a plurality of elements protruding from and fixedly attached to the mounting structure wherein each of the elements has a top face opposite the mounting surface, said top face has an undulating shape with a plurality of peaks, each peak having a summit and downwardly sloping sides, and wherein the elements are longitudinally spaced apart from each other on the mounting structure.

2. The device of claim 1 wherein each segment includes a first end and a second end opposite the first end and the linking means comprises:

a first connection strip at the first end of the segment; and a second connection strip at the second end of the segment.

3. The device of claim 2 wherein:

the first connection strip comprises two pins and two holes; and the second connection strip comprises a surface defining two pairs of holes wherein the segments may be connected by causing the pins of one segment to be fitted into the holes defined in the second connection strip of the connected segment.

4. The device of claim 1 wherein the linking means comprises a casing for supporting a plurality of segments and further comprising at least one elongated fastener strap connected to the casing.

5. The device of claim 1 wherein each segment includes a first end and a second end opposite the first end and the linking means comprises:

a first connection strip at the first end of the segment; and a second connection strip at the second end wherein segments may be linked together by connecting the first connection strip of one segment to the second connection strip of another segment to form any desired length of segments; and a casing for supporting a plurality of segments wherein the linked segments are placed into the casing.

6. The device of claim 5 further comprising at least one fastener strap secured to the casing.

7. The device of claim 1 wherein the mounting structure is made of a flexible material such that the segments conform to the shape of the body upon which they are fastened.

* * * * *